(12) United States Patent
Ye et al.

(10) Patent No.: US 12,342,057 B2
(45) Date of Patent: Jun. 24, 2025

(54) ADAPTIVE USER INTERFACE OVERLAY SYSTEM AND METHOD FOR X-RAY IMAGING SYSTEM

(71) Applicant: GE Precision Healthcare LLC, Wauwatosa, WI (US)

(72) Inventors: Minghui Ye, Beijing (CN); Vishal Raghavan, Chennai (IN); Rakesh S. Bhat, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 323 days.

(21) Appl. No.: 18/110,068

(22) Filed: Feb. 15, 2023

(65) Prior Publication Data

US 2024/0276081 A1 Aug. 15, 2024

(51) Int. Cl.
*H04N 23/30* (2023.01)
*A61B 6/00* (2024.01)
(Continued)

(52) U.S. Cl.
CPC .......... *H04N 23/30* (2023.01); *A61B 6/0407* (2013.01); *A61B 6/488* (2013.01); *H04N 9/646* (2013.01);
(Continued)

(58) Field of Classification Search
CPC ...... H04N 23/30; H04N 9/646; H04N 23/635; H04N 23/64; H04N 23/85; H04N 9/64;
(Continued)

(56) References Cited

U.S. PATENT DOCUMENTS 6,486,894 B1 11/2002 Abdelhadi et al.
9,658,736 B2 5/2017 Frem et al.
(Continued)

FOREIGN PATENT DOCUMENTS

CN 109840041 A 6/2019
JP 2004165986 A 6/2004

OTHER PUBLICATIONS

Yang-Kyun Park et al., Gain Correction for an X-ray Imaging System with a Movable Flat Panel Detector and Intrinsic Localization Crosshair, Technology in Cancer Research & Treatment, Apr. 2016, pp. 387-395, vol. 15, Issue 2.

*Primary Examiner* — Sath V Perungavoor
*Assistant Examiner* — Tyler B Edwards
(74) *Attorney, Agent, or Firm* — Boyle Frederickson S.C.

(57) ABSTRACT

According to one aspect of an exemplary embodiment of the disclosure, a system and method for adaptively altering the presentation color for an overlay to be presented along with a camera image on a display of a radiography system includes the steps of providing an imaging system having a radiation source, a detector, and a camera aligned with the detector. A control processing unit including image processing circuitry is operably connected to the camera to generate a camera image(s) of the subject and the detector. The camera image analyzed by the image processing circuitry to determine the region of interest (ROI) within the camera image and the dominant color(s) present in the ROI, such that presentation color for the overlay can be automatically adjusted to a complementary color for monochromatic camera images or to a high contrast color for chromatic camera images to increase the visibility of the overlay.

20 Claims, 8 Drawing Sheets

(51) Int. Cl.
 *A61B 6/04* (2006.01)
 *H04N 9/64* (2023.01)
 *H04N 23/60* (2023.01)
 *H04N 23/63* (2023.01)
 *H04N 23/85* (2023.01)

(52) U.S. Cl.
 CPC .......... *H04N 23/635* (2023.01); *H04N 23/64* (2023.01); *H04N 23/85* (2023.01)

(58) Field of Classification Search
 CPC ..... A61B 6/0407; A61B 6/488; A61B 6/5211; A61B 6/469
 See application file for complete search history.

(56) References Cited

U.S. PATENT DOCUMENTS

| | | | |
|---|---|---|---|
| 2015/0228086 A1* | 8/2015 | Maurer | H04N 23/635 382/100 |
| 2019/0066260 A1* | 2/2019 | Suehling | A61B 6/461 |
| 2022/0270535 A1 | 8/2022 | Chiang et al. | |

* cited by examiner

ADAPTIVE USER INTERFACE OVERLAY SYSTEM AND METHOD FOR X-RAY IMAGING SYSTEM

FIELD OF THE DISCLOSURE

The subject matter disclosed herein generally relates to X-ray imaging systems. More specifically, the subject matter relates to systems and methods for presenting information on a user interface.

BACKGROUND OF THE DISCLOSURE

X-ray systems, such as digital radiography (RAD) systems, mammography systems, computed tomography systems, and the like are used to generate images showing internal features of a subject. In the medical context, such imaging systems are used for viewing internal anatomies and tissues, such as for diagnostic purposes. In modern projection X-ray systems, for example, X-rays are generated by an X-ray source and are directed towards a patient or other subject. The X-rays transfer through the subject, and are absorbed or attenuated by internal features. The resulting X-rays impact a digital detector where image data is generated. Collecting the image data allows for reconstruction of a useful image. Similar techniques are used for mammography, computed tomography, fluoroscopy and tomosynthesis image generation.

It is a general goal in radiography to acquire sufficient image data for reconstruction of a useful image, while optimizing, and often minimizing the dosage of radiation to the patient. Various techniques have been developed to obtain these goals. In one manner of accomplishing this goal, the imaging system utilized can employ a camera to obtain a camera image of the patient to be imaged. The camera image can be obtained by the camera in real-time, such as in a streaming process where camera images are continuously obtained by the camera and presented in a viewable manner to the user of the imaging system. In one embodiment, the imaging system presents a real time camera image of the anatomy of the patient to be imaged using the radiography imaging system on a user interface, such as a display forming a part of the imaging system. On the user interface, the camera image is displayed along with various types of overlays and annotations concerning information generated by the imaging system, including but not limited to a representation of a central point the field of view (FOV) of the imaging system on the patient anatomy shown in the camera image, the border of the detector, and/or the locations of components of the imaging system positioned behind the patient anatomy, such as an ionization chamber, among others. In this manner, the camera image provides a user with a visual representation of both the patient anatomy and imaging system to greatly assist in the proper positioning of the patient anatomy prior to initiating an imaging procedure. In this manner, the patient can be located properly with respect to the imaging system to obtain the correct view of the patient anatomy, thus avoiding improper positioning and unnecessary retakes to minimize the radiation dose to the patient.

Problems arise, however, as a result of the default form, e.g., color, of the overlays and indications presented on the camera image on the display for the imaging system. As shown in FIGS. 1A and 1B, the default color for the overlay/indication 1000 of the field of view of the imaging system presented on the camera image 1002 can be obscured in whole or in part as a result of the colors of the clothing 1004 worn by the patient 1006 in the camera image 1002 that form the background for the overlay/indications 1000 in the displayed camera image 1004. In FIG. 1A, the color of the clothing 1004 closely approximates the default color of the overlay/indication 1000, i.e., the clothing is approximately mono-chromatic relative to the color for the overlay/indications 1000, such that all portions of the overlay/indication 1000 presented within the boundary of the clothing 1004 are effectively rendered invisible within the displayed camera image 1002. On the opposed end of the spectrum, as shown in FIG. 1B, when the clothing 1004 is highly chromatic in nature, the highly contrasting or messy background provided by the clothing 1004 also renders the overlay/indications 1000 very difficult to discern by user of the imaging system. Therefore, although the overlay/indication(s) 1000 provide the necessary information in the camera image 1002 on the display regarding the proper position of the patient relative to the components of the imaging system, the patient can oftentimes be placed in an incorrect location due to the inability of the user to discern the overlay/indication(s) 1000 on the camera image 1002, causing unnecessary retakes of the image and increased radiation doses to the patient 1006.

In an attempt to address this issue, certain prior art imaging systems provide the user with the ability to alter the color for the presentation of the overlay and/or indication(s) to improve the visibility of the overlay and/or indication(s) within the displayed camera image. However, the effectiveness of the selected color change is highly dependent upon the subjective perception of the user regarding the appropriate color for the presentation of the overlay and/or indication(s) in view of the background, e.g., clothing worn by the patient, in the camera image. Further, as the selection of the color change is performed by the user, in many occasions the user will simply forego the selection of an alternate color for the overlay and/or indication(s) to avoid taking more time for the set up of the imaging procedure, and will rely on their subjective ability to properly discern the locations and information provided by the overlay and/or indication(s) presented on the camera image. In each situation, the use of subjective criteria by the user for the alteration or non-alteration of the color for the presentation of the overlay and/or indication(s) does not significantly lessen the potential for inaccurate positioning of the patient in the subsequent imaging procedure.

Therefore, with regard to each of the aforementioned shortcomings of prior art imaging systems concerning the ability of those imaging systems to display the overlay and/or indication(s) in a readily discernable manner on the display for the imaging system, it is desirable to develop an improved system and method for the adapting the presentation of the overlay and/or indication(s) provided on the display of the imaging system.

SUMMARY OF THE DISCLOSURE

According to one aspect of an exemplary embodiment of the disclosure, a method for adaptively adjusting a presentation color of an overlay in conjunction with a camera image presented on a user interface of a radiography imaging system includes the steps of providing an imaging system having a radiation source, a detector alignable with the radiation source, the detector having a support on or against which a subject to be imaged is adapted to be positioned, a camera aligned with the detector, a control processing unit operably connected to the radiation source and detector to generate image data in an imaging procedure performed by the imaging system, and to the camera to generate camera images, the control processing unit including image processing circuitry and an interconnected database for processing the image data from the camera to create one or more camera images of the detector, a display operably connected to the controller for presenting information to a user, and a user interface operably connected to the control processing unit to enable user input to the control processing unit, positioning the subject between the radiation source and the detector, operating the camera to generate a camera image of at least one of the subject, the detector and combinations thereof, determining an ROI within the camera image, determining a dominant color of the ROI, and adjusting a presentation color of an overlay presented with the camera image on the display in relation to the dominant color of the ROI.

According to another aspect of an exemplary embodiment of the disclosure, a radiography imaging system includes a radiation source, a detector alignable with the radiation source, a camera alignable with the detector, a control processing unit operably connected to the radiation source and detector to generate image data in an imaging procedure performed by the imaging system, and to the camera to generate camera images, the control processing unit including image processing circuitry and an interconnected database for processing the image data from the camera to create one or more camera images of the detector, a display operably connected to the controller for presenting information to a user, and a user interface operably connected to the control processing unit to enable user input to the control processing unit, wherein the image processing circuitry is configured to operate the camera to generate a camera image of at least one of the subject, the detector and combinations thereof, to determine an ROI within the camera image, to determine a dominant color of the ROI, and to adjust a presentation color of an overlay presented with the camera image on the display in relation to the dominant color of the ROI.

These and other exemplary aspects, features and advantages of the invention will be made apparent from the following detailed description taken together with the drawing figures.

BRIEF DESCRIPTION OF THE DRAWINGS

These and other features, aspects, and advantages of the present invention will become better understood when the following detailed description is read with reference to the accompanying drawings that illustrate the best mode currently contemplated of practicing the present disclosure and in which like characters represent like parts throughout the drawings, wherein.

DETAILED DESCRIPTION OF THE DRAWINGS

Figure 1A:
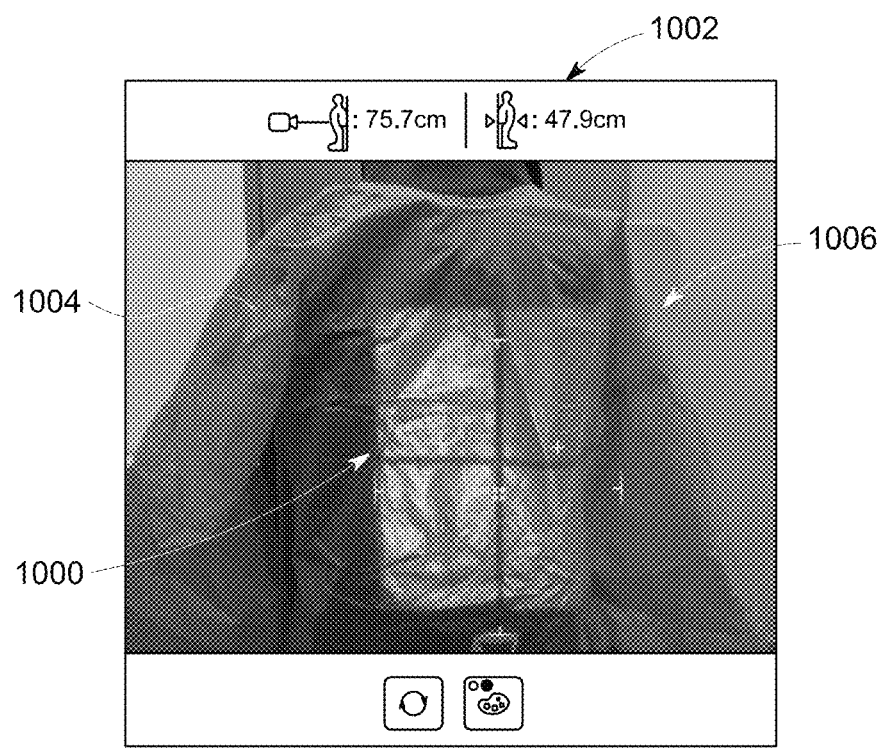
FIG. 1A is a schematic view of a prior art camera image including a monochromatic background for the presentation of an overlay/indication on the camera image.
Figure 1B:
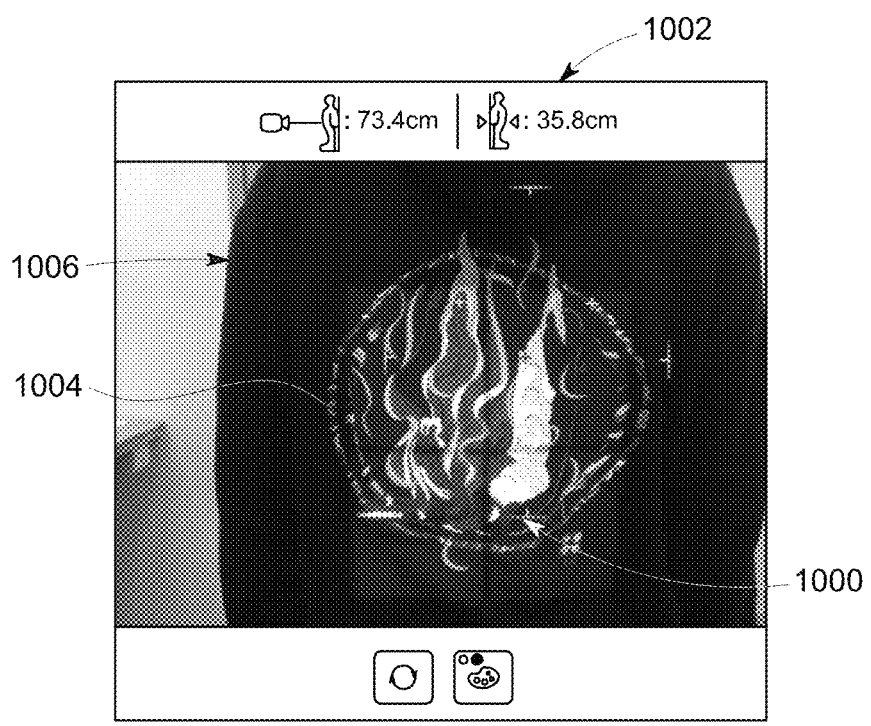
FIG. 1B is a schematic view of a prior art camera image including a highly chromatic background for the presentation of an overlay/indication on the camera image.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Certain examples provide an image processing apparatus including an artificial intelligence system (AI system). The AI system can detect, segment, and quantify colors present within a camera image, for example. The AI system can be a discrete output of positive or negative for a finding, a segmentation, etc. For example, the AI system can instantiate machine learning and/or other artificial intelligence to detect, segment, and analyze the colors present within a camera image provided to the AI system. For example, the AI system can instantiate machine learning and/or other artificial intelligence to detect the nature of a background of a camera image provided by a camera operably connected to the imaging system, to determine the number and/or type of colors present within the camera image, to determine the presence of any dominant color in the camera image, and to adapt the color for the presentation of an overlay and/or indication on the camera image top maximize the visibility of the overlay and/or indication within the camera image.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

Certain examples use neural networks and/or other machine learning to implement a new workflow for image and associated patient analysis including automated alteration of the display of images and associated information generated and delivered at the point of care of a radiology exam. Certain examples use Artificial Intelligence (AI) algorithms to process one or more camera images obtained during one or more imaging exams (e.g., an image or set of images), and provide an overlay for the camera image(s) presented on a display to improve the ability of the user to discern the information provided by the overlay. The overlay (e.g., including detector border information, FOV center information, ionization chamber location information, etc.) may be intended for the technologist acquiring the exam, clinical team providers (e.g., nurse, doctor, etc.), radiologist, administration, operations, and/or even the patient. The overlay may be to indicate a specific or multiple quality control and/or radiological finding(s) or lack thereof, for example, with regard to the positioning of the patient relative to the detector and/or ionization chambers.

In certain examples, the AI algorithm can be (1) embedded within an imaging device, (2) running on a mobile device (e.g., a tablet, smart phone, laptop, other handheld or mobile computing device, etc.), and/or (3) running in a cloud (e.g., on premise or off premise) and delivers the alert via a web browser (e.g., which may appear on the radiology system, mobile device, computer, etc.). Such configurations can be vendor neutral and compatible with legacy imaging systems. For example, if the AI processor is running on a mobile device and/or in the "cloud", the configuration can receive the images (A) from the x-ray and/or other imaging system directly (e.g., set up as secondary push destination such as a Digital Imaging and Communications in Medicine (DICOM) node, etc.), (B) by tapping into a Picture Archiving and Communication System (PACS) destination for redundant image access, (C) by retrieving image data via a sniffer methodology (e.g., to pull a DICOM image off the system once it is generated), etc.

Certain examples provide apparatus, systems, methods, etc., to provide an adaptive overlay for a camera image presented on a display based on output of an algorithm instantiated using and/or driven by an artificial intelligence (AI) model, such as a deep learning network model, machine learning network model, etc. For example, the presentation of the overlay can be altered to provide a more easily viewable overlay for the camera image based on an output of an AI algorithm.

The techniques describe herein provide a mechanism to determine if a predetermined color for an overlay to be presented in conjunction with one or more camera images of a patient will make the overlay difficult to discern when placed over the camera image. The ability of the algorithm/AI to adaptively determine a readily discernable color for the overlay for presentation on the camera image enables a clear understanding of the information provided in the overlay regarding the patient position relative to the detector and/or elements thereof, which allows for more accurate or proper positioning of the patient relative to the detector prior to initiating an imaging procedure and significantly lessening the need for retakes and the consequent increased radiation dosage to the patient.

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include colors, objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, classified and further annotated for object localization, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), visible light or camera images, etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

Figure 2:
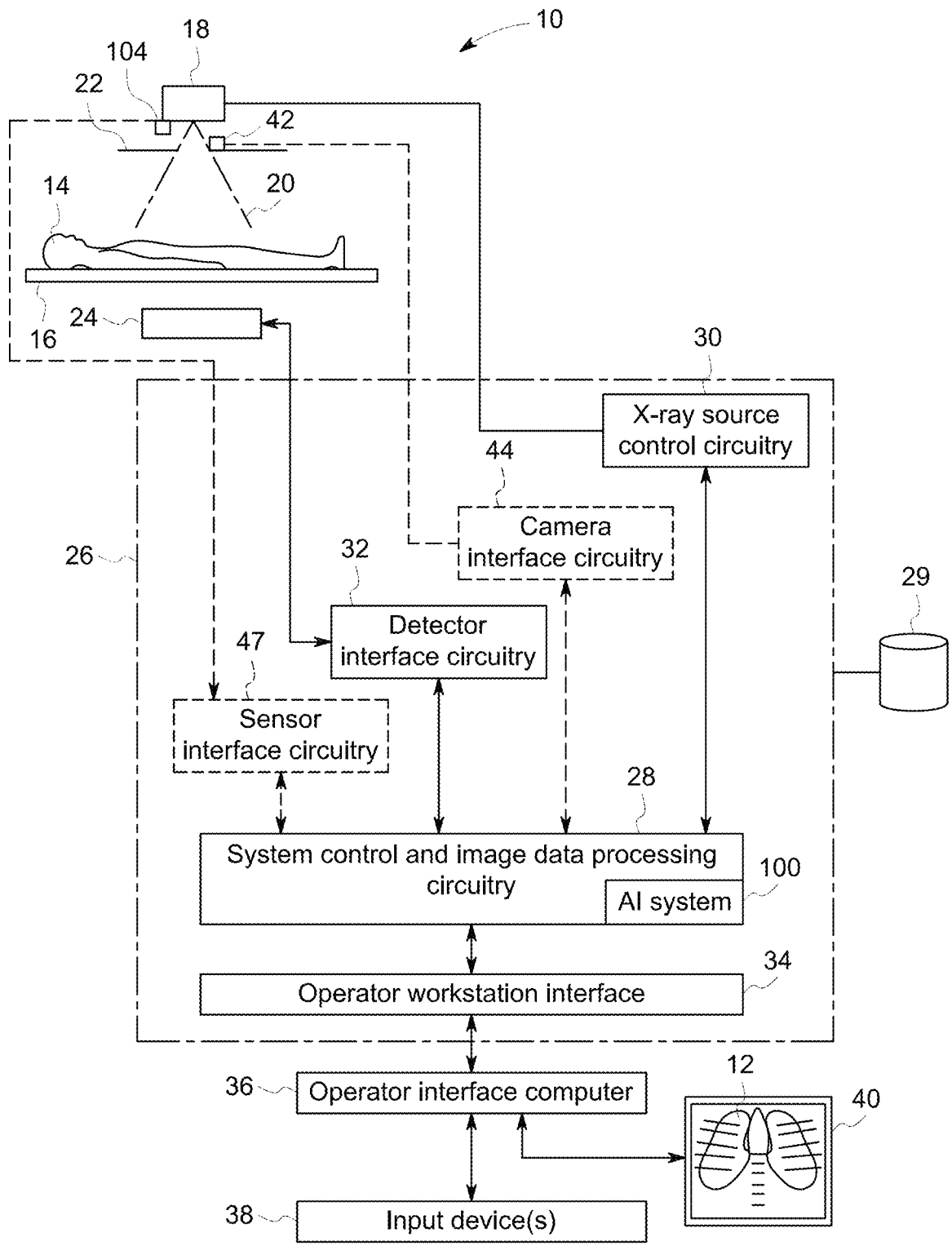
FIG. 2 is a diagrammatical representation of an X-ray imaging system including an adaptive user interface overlay display system according to an exemplary embodiment of the disclosure.

Referring to FIG. 2, an imaging system, such as a radiography imaging system including, but not limited to an X-ray imaging system 10 is illustrated. The X-ray imaging system 10, such as that disclosed in US Patent Application Publication No. 2012/0128125, entitled Region Of Interest Determination For X-Ray Imaging, which is expressly incorporated herein by reference for all purposes, is adapted for generating images 12 of a subject 14. In a medical diagnostic context, the subject 14 may be positioned on a support 16. An X-ray source 18 is adapted to produce a beam of radiation 20 which passes through collimator 22. The radiation traverses the subject, with some of the radiation being attenuated or absorbed, and resulting radiation impacting a detector 24. Alternatively, the system 10 can be a mobile RAD system, and/or the subject 14 can be located in a standing position in front of the detector in a digital radiography (RAD) imaging system as disclosed in US Patent Application Publication No. 2021/0183055, entitled Methods And Systems For Analyzing Diagnostic Images, which is expressly incorporated herein by reference in its entirety for all purposes.

A controller/control processing system/control processing unit/processor 26 is coupled to both the radiation source 18 and the detector 24. In general, this system 26 allows for regulation of operation of both the source 18 and the detector 24, and permits collection of information from the detector 24 for reconstruction of useful images. In the illustrated embodiment, for example, the control and processing unit/system or controller 26 includes a system control and image processing circuitry/unit 28. Such circuitry 28 will typically include a programmed processor, supporting memory/database 29, and specific applications executed by the processor during operation, which may be stored in memory/database 29 along with executable instructions for the operation of circuitry 28 and the control processing unit/controller 26, and so forth. The circuitry 28 will be coupled to X-ray source control circuitry 30 that itself allows for control of operation of the X-ray source 18. The X-ray source control circuitry 30 may, for example, under the direction of the system control and image data processing circuitry 28, regulate the current and voltage applied to the X-ray source 18, alter the configuration of the collimator 20, trigger the generation of X-rays from the source 18, trigger startup and shutdown sequences of the source, and so forth.

The system control and image data processing circuitry/processing unit/processor or circuitry 28 is further coupled to detector interface circuitry 32. This circuitry 32 allows for enabling the digital detector 24, and for collecting data from the digital detector 24. As will be appreciated by those skilled in the art, various designs and operations of such detectors 24 and detector interface circuitry 32 are known and are presently in use. Such designs will typically include detectors 24 having an array of discrete pixel elements defined by solid state switches and photodiodes. The impacting radiation affects the charge of the photodiodes, and the switches allow for collection of data/information regarding the impacting radiation (e.g., depletion of charge of the photodiodes). The data/information may then be processed to develop detailed images in which gray levels or other features of individual pixels in an image are indicative of the radiation impacting corresponding regions of the detector 24.

The control processing unit 26 is also illustrated as including an operator workstation interface 34. This interface allows for interaction by an operator who will typically provide inputs through an operator interface computer 36. The operator interface computer 36 and/or the system control and image data processing circuitry 28 may perform filtering functions, control functions, image reconstruction functions, and so forth. One or more input devices 38 are coupled to the operator interface computer 36, such as a keyboard, a stylus, a computer mouse, combinations thereof, among other suitable devices. The operator interface computer 36 is further coupled to a display or monitor 40 on which images may be displayed, instructions may be provided, regions of interest (ROIs) may be defined as discussed below, and so forth. In general, the operator interface computer 36 may include memory and programs sufficient for displaying the desired images, and for performing certain manipulative functions, in particular the definition of a region of interest (ROI) for image exposure control.

It should be noted that, while through the present discussion reference is made to an X-ray system 10 in the medical diagnostic context, the present invention is not so limited. For example, the invention may be used for other radiological applications, such as fluoroscopy, computed tomography, tomosynthesis and so forth. The system 10 may be used in other application contexts as well, such as part and parcel inspection, screening and so forth. Moreover, in certain contexts, and certain aspects of the detectors may be used with non-digital detectors, such as conventional film.

Figure 3:
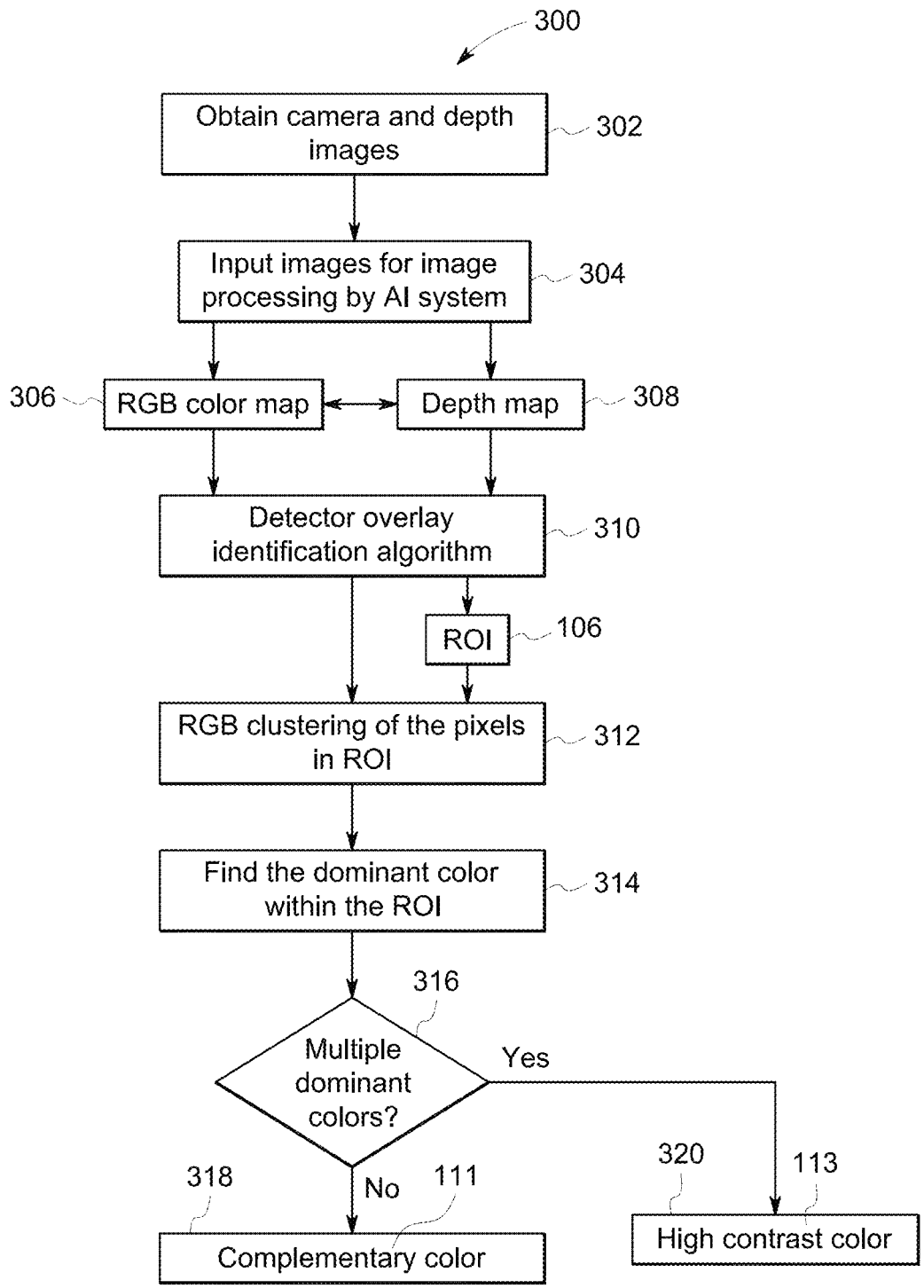
FIG. 3 is a flowchart illustrating a method of operation of the adaptive user interface overlay display system of FIG. 2 to determine an optimized overlay for presentation to a user according to an exemplary embodiment of the disclosure.

The system illustrated in FIGS. 2 and 3 is adapted to allow for selection or definition of a region of interest (ROI) that will serve for exposure control during imaging sequences. In the particular embodiment illustrated, a camera 42 may be positioned above the patient and coupled to camera interface circuitry 44. It is contemplated that the camera 42 may be used to generate one or more images 46 (FIG. 3) of the subject 14 that can form the basis for operator definition of a region of interest (ROI) as described below. The camera 42 can have any suitable form, such as an RGB camera or device. The camera interface circuitry 44 allows for triggering the camera 42 to collect a camera image data/image(s) 46 that can be processed by the camera interface circuitry 44 and forwarded to the system control and image data processing circuitry 28. The image 46 may then be conveyed to the operator interface computer 36 and displayed on the monitor 40. Further, the camera 42 can collect the camera image data/image(s) 46 in a continuous or streaming manner, such that the camera 42 operates in the manner of or can be formed as a video camera, to obtain the camera image data/image(s) 46 in real-time for presentation in a continuous, real-time manner on the display or monitor 40. The camera image data/image(s) 46 are presented on the display 40 along with an overlay 48 that includes various indications 50, such as a center field of view crosshairs 52, detector border indicators 54, and ionization chamber location indicators 56, among others, and other relevant information 58 regarding the patient 14 and/or imaging procedure to be performed.

Looking again at FIG. 2, one specific component or application of the system control and image processing circuitry 28 is an adaptive user interface (UI) overlay algorithm or artificial intelligence (AI) 100 which may be stored in memory/database 29 along with executable instructions for the operation of the AI 100.

According to an exemplary embodiment for the automatic analysis and adaptation of the presentation of the overlay 48 on the camera image 46 on the display 40 by the adaptive overlay AI system 100, the process performed by the AI system 100 may be accomplished using Artificial Intelligence (AI) based approaches like machine learning (ML) or deep learning (DL), which can automatically categorize the individual frames into various categories. With AI based implementation, the problem of determining the colors present in the camera image 46 may be formulated as a classification problem. Convolutional neural networks (CNN) a class of DL based networks, which are capable of handling images by design can be used for color classification achieving very good accuracies. Also recurrent neural networks (RNN) and their variants like long short term memory (LSTM) and gated recurrent units (GRU), which are used with sequential data can also be adapted and combined with CNNs to classify individual colors within the camera images 46. ML based approaches like support vector machine, random forest, etc., can be also be used for color classification, though their performance as well as their adaptability to varying imaging conditions are pretty low when compared to the DL based methods. Any suitable optimization algorithm, for example gradient descent or root mean square propagation (RMSprop) or adaptive gradient (AdaGrad) or adaptive moment estimation (Adam) or others (normally used with DL based approaches), that minimizes the loss function for classification could further be used to perform the model training with annotated training data. Once trained, the model can be used to perform inference on new unseen images (image frames not used for model training), thereby classifying the color present in each camera image 46 into one of the available categories with which the model was trained on.

FIG. 3 schematically illustrates the method 300 employed by the system control and image processing circuitry 28 and/or the AI system 100 to analyze the camera image 46 and adapt the presentation of the overlay 48 for best viewability in the user interface (UI)/display 40. In step 302, the camera 42 is operated by the camera interface circuitry 44 to obtain a color camera image 46 of the patient 14 in a position adjacent the detector 28, e.g., where the patient 14 is positioned between the radiation source 18 and the detector 24 in preparation for the performance of an imaging procedure using the imaging system 10.

In step 304, utilizing the camera image 46 as the input, the system control and image processing circuitry 28 and/or the AI system 100 determines a color map 306 and a depth map 308 using known processes. The color map 306 created by the AI system 100 provides a representation of all of the colors detected by the image processing circuitry 28/AI system 100 within the pixels of entire camera image 46. The depth map 308 created by the image processing circuitry 28/AI system 100 utilizes the color camera image 46 and a depth image 102 to provide a representation of the position of the patient 14 relative to the detector 24 based on the determined distances of each pixel in the camera image 46 from a comparison and/or matching with corresponding pixels in the depth image 102. The camera image 46 and the depth image 102 can be obtained separately, with the camera image 46 obtained by the camera 42, e.g., an RGB camera, and the depth image 102 can be obtained from a suitable depth sensor 104 (FIG. 2), such as a time-of-flight sensor, or Lidar sensor, disposed adjacent the camera 42 and operably connected to the sensor interface circuitry 47 within the control processing unit 26. Alternatively, the camera 42 can be an RGB-D camera that is capable of obtaining both the RGB camera image 46 and the depth image 102, i.e., the RGB-D camera can function as the camera 42 and the depth sensor 104, or can optionally used with a separate camera 42.

Figure 4:
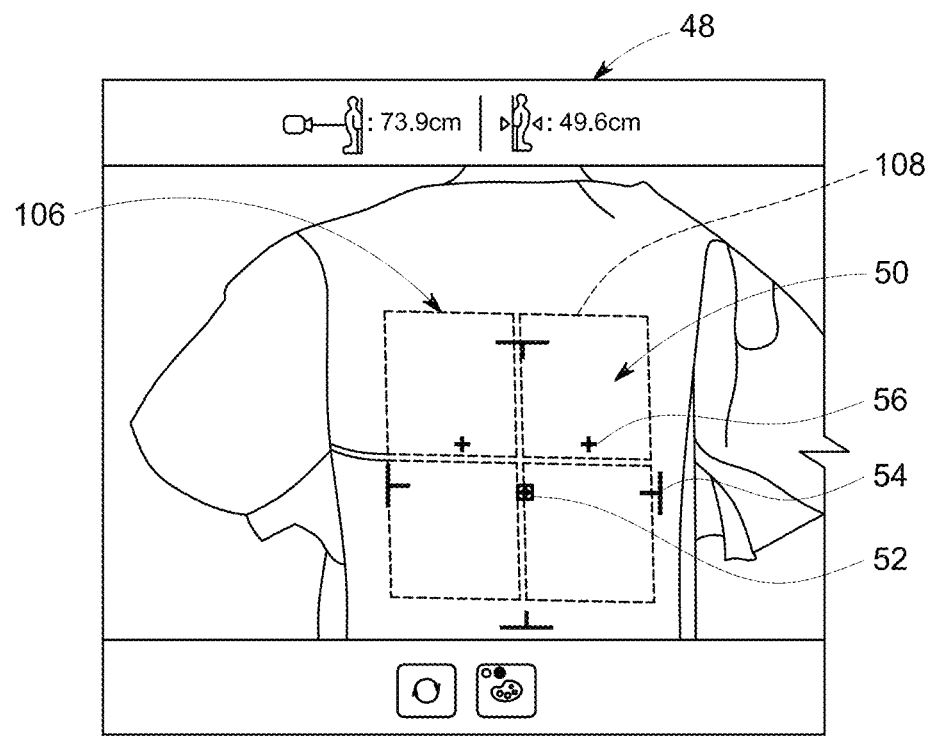
FIG. 4 is a schematic view of a camera image obtained by the X-ray system of FIG. 2 including an indication of the ROI of the camera image according to an exemplary embodiment of the disclosure.
Figure 5:
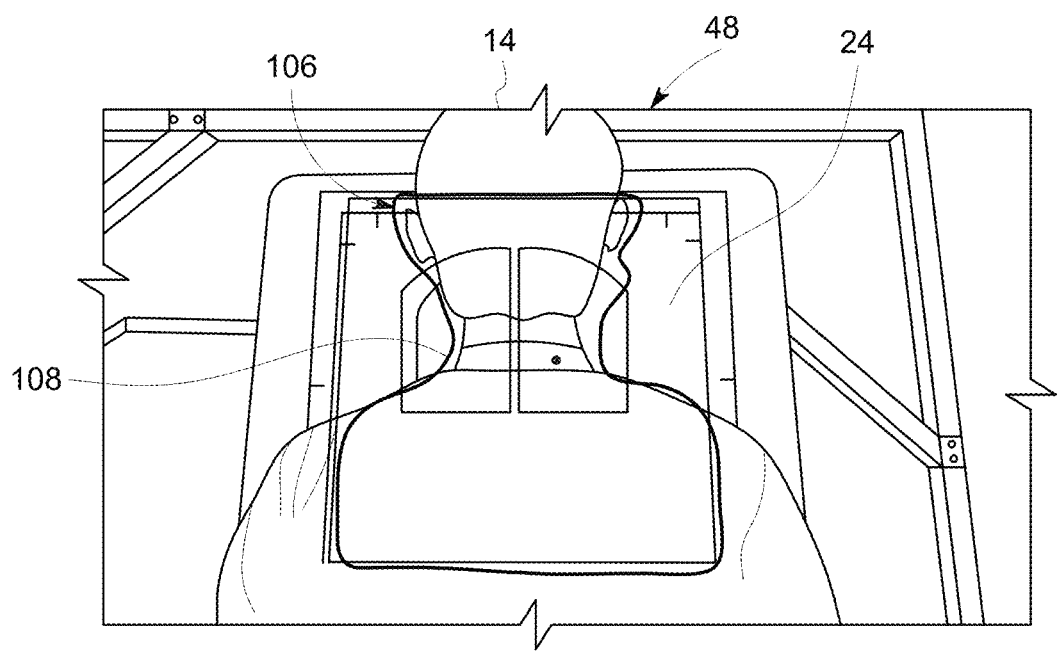
FIG. 5 is a schematic view of a camera image obtained by the X-ray system of FIG. 2 including an indication of the ROI of the camera image according to an exemplary embodiment of the disclosure.

In step 310, the image processing circuitry 28 and/or the AI system 100 identifies the region of interest (ROI) 106 defined by the boundary 108 of the detector 24 within the camera image 46 and the depth image 102, such as through the use of a detector overlay identification algorithm (not shown) formed as part of the image processing circuitry 28 and/or the AI system 100 to determine the corresponding boundary for the overlay 48 to be presented with the camera image 46. In one embodiment, as shown in FIG. 4, where the entire detector 24 is covered by the patient 14, the ROI 106 can be defined by the image processing circuitry 28 and/or the AI system 100 as the entire area within the boundary 108. Alternatively, as shown in FIG. 5, where the patient 14 covers only a portion of the detector 24, the ROI 106 can be defined by the area of the detector 24 covered by the patient 14 within the boundary 108, such that any areas of the detector 24 that are exposed are not considered in further processing of the camera image 46 by the image processing circuitry 28 and/or the AI system 100.

After the determination of the ROI 106, in step 312 the image processing circuitry 28 and/or the AI system 100 proceeds to employ the color map 306 to the ROI 106 in order to determine the different colors 110 present within the ROI 106. In one exemplary embodiment for performing this analysis, the image processing circuitry 28 and/or the AI system 100 clusters the pixels of similar colors 110 within the coordinates of the color map 306 defined by the determined ROI 106 to determine all the colors 110 present in the ROI 106. To increase the speed and ease of this processing by the image processing circuitry 28 and/or the AI system 100, the image processing circuitry 28 and/or the AI system 100 clusters the RGB colors 110, e.g., to the nearest twenty (20) values of the respective R, G and B, to prevent illumination/noise from classifying different shades of the same color 110 differently. For example, a patient 14 wearing clothing within the defined ROI 106 that would normally be classified as RGB (0,0,0) can be interpreted as RGB (0,0,5) and RGB (0,0,10) at different points within the ROI 106 due to any illumination and/or noise present within the camera image 46. Therefore, to simplify the analysis and speed up the processing of the camera image 46 by the image processing circuitry 28 and/or the AI system 100, particularly in situations where the camera images 46 are provided in real-time, e.g., in the form of streaming images or a streaming video, the clustering of the colors 110 according to the user or system-defined clustering parameters or predetermined ranges is performed. The parameters or predetermined ranges for the clustering of the colors 110 can be selected as desired in order to limit the number of colors 110 to be identified by the image processing circuitry 28 and/or the AI system 100, such as limiting to 25 or fewer colors 110, limiting to 15 or fewer colors 110, limiting to 10 or fewer colors 110, or limiting to 5 or fewer colors 110, among other suitable exemplary embodiments, and consequently enable faster analysis and processing of the images or video by the image processing circuitry 28 and/or the AI system 100.

Figure 6:
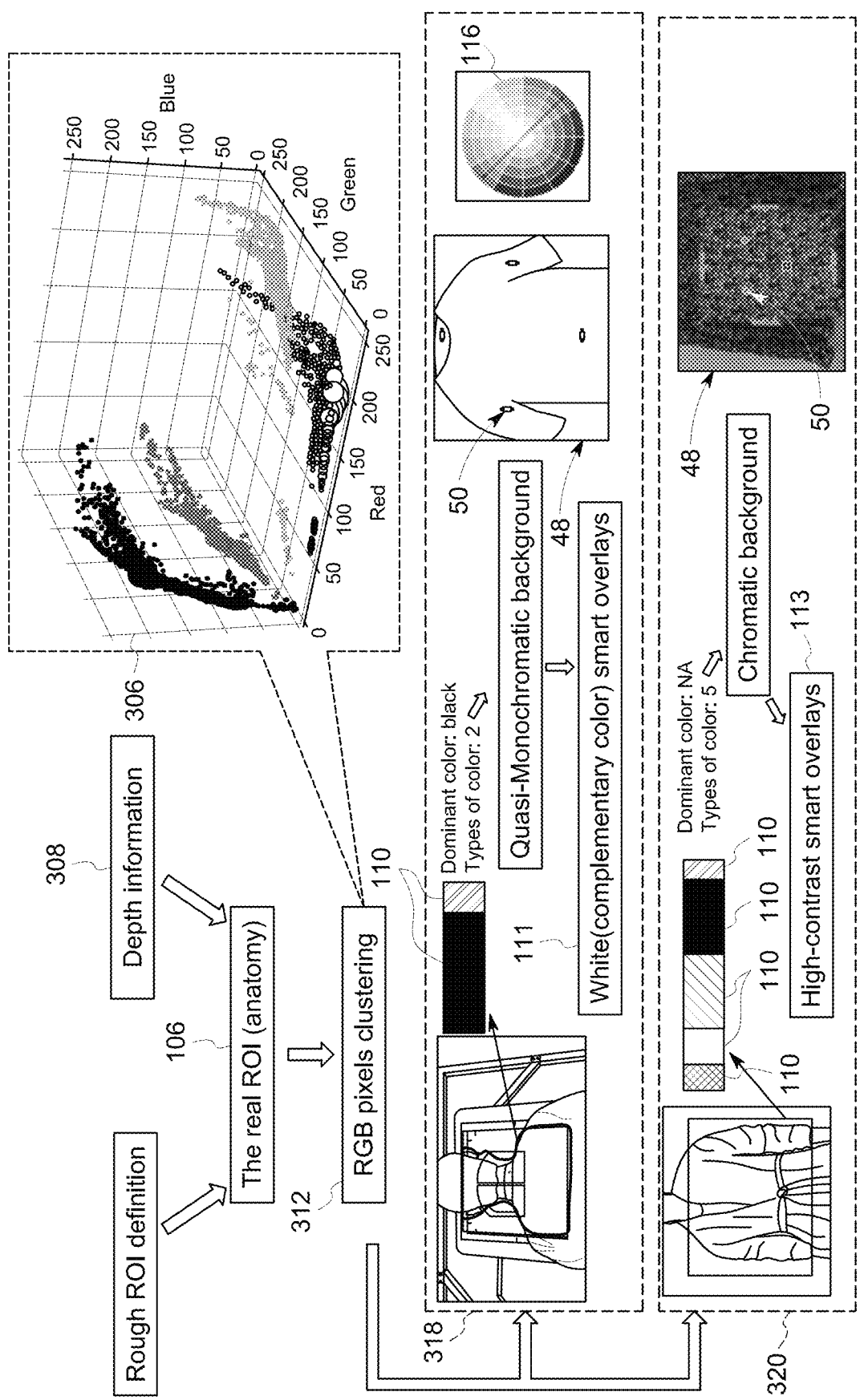
FIG. 6 is a schematic view of the operation of the adaptive user interface overlay display system in the method of FIG. 3 according to an exemplary embodiment of the disclosure.

After the determination and clustering of the different colors 110 present in the ROI 106, in step 314 the image processing circuitry 28 and/or the AI system 100 proceeds to determine the dominant color 110 present within the ROI 106. This determination can be performed in any number of suitable different manners, such as simply aggregating the pixels in the camera image 46 corresponding to each of the detected colors 110, and subsequently calculating a percentage of the camera image 46 that is made up of the pixels of each color 110. Once the percentages of each color 110 present have be determined, to determine the dominant color 110 within the camera image 46, the image processing circuitry 28 and/or the AI system 100 compares the percentages of each color 110 present in the camera image 46 with a user- or system-predetermined threshold for a dominant color 110 and/or with one another. In one exemplary embodiment, the comparison of the percentages of the respective colors 110 can be made using a determination of the difference in the absolute values of the determined percentages for each color 110, e.g., if the percentage of one color 110 in the ROI 106 is more than 1.5-2 times the percentage of the other color 110 in the ROI 106. For example, as shown in FIG. 6, in the situation where two colors 110 are present in the ROI 106, and the percentage or amount of the first color 110 is approximately 4 times the amount or percentage of the second color 110, the image processing circuitry 28 and/or the AI system 100 can determine that the first color 110 is the dominant color in the ROI. Conversely, as also shown in FIG. 6, where two or more colors 110 are determined to have relative amounts or percentages that are close to one another, e.g. within ±5% of one another, each of these colors 110 can be classified as being dominant within the ROI 106.

In step 316, in reviewing the dominant color determination of step 314, the image processing circuitry 28 and/or the AI system 100 determines the number of dominant colors 110 that are present within the ROI 106 in order to determine a presentation color 111,113 for the overlay 48. If only one dominant color 110 was detected, the image processing circuitry 28 and/or the AI system 100 classifies the camera image 46 as a monochromatic or quasi-monochromatic background and proceeds to step 318 for the selection of a complementary color 111 to the dominant color 110 for use in the overlay 48. In contrast, if more than one dominant color 110 has been determined to be present, the image processing circuitry 28 and/or the AI system 100 classifies the camera image 46 as a chromatic background and proceeds to step 320 to employ a high contrast color 113 for use in the overlay 48.

Figure 7A:
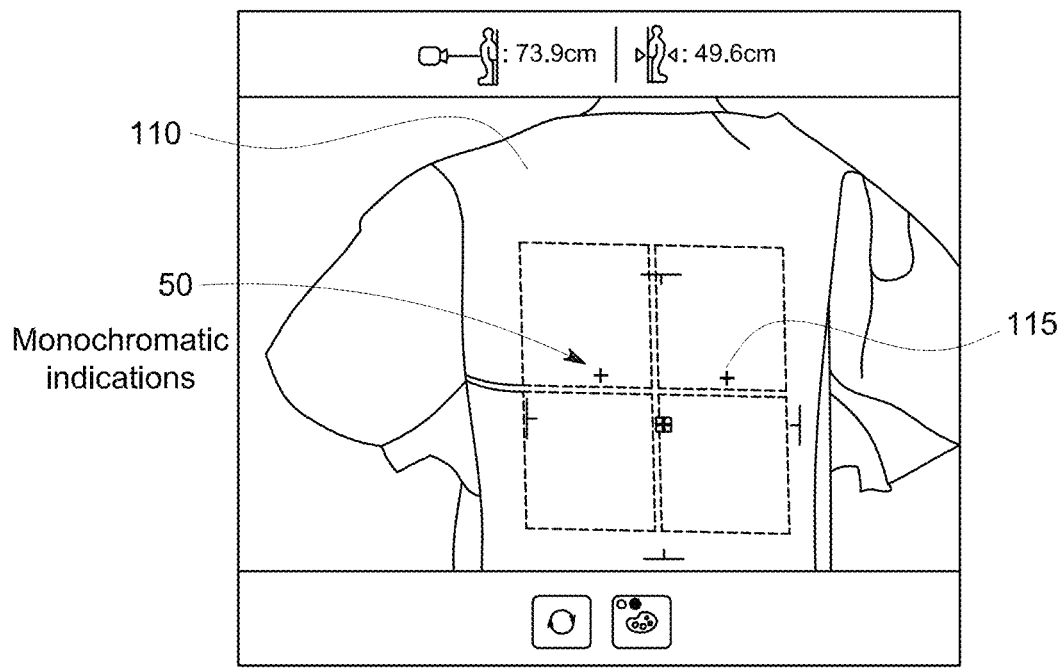
FIGS. 7A-7D are schematic views of camera images including conventional overlay and overlays formed by the adaptive user interface overlay display system according to an exemplary embodiment of the disclosure.
Figure 7B:
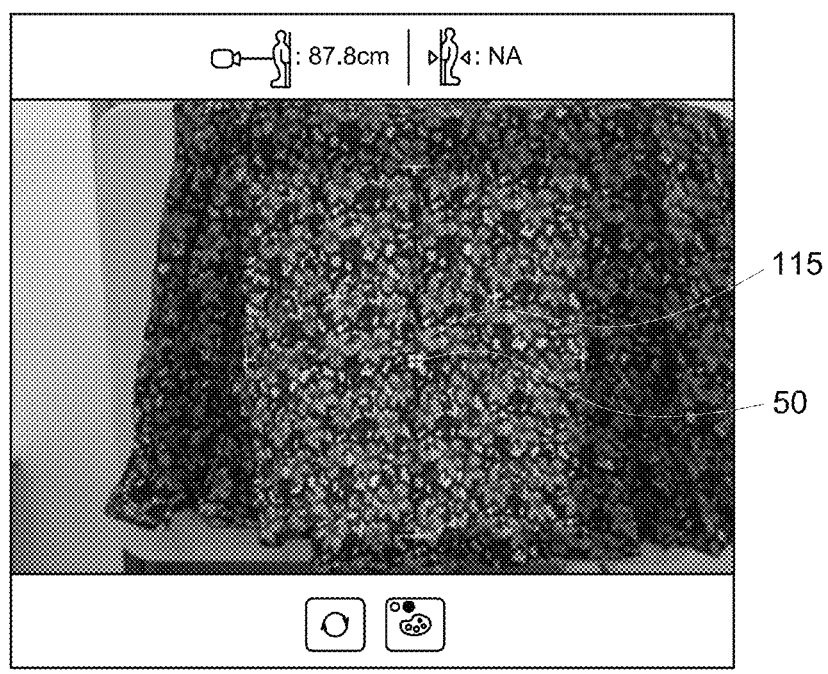
Figure 7C:
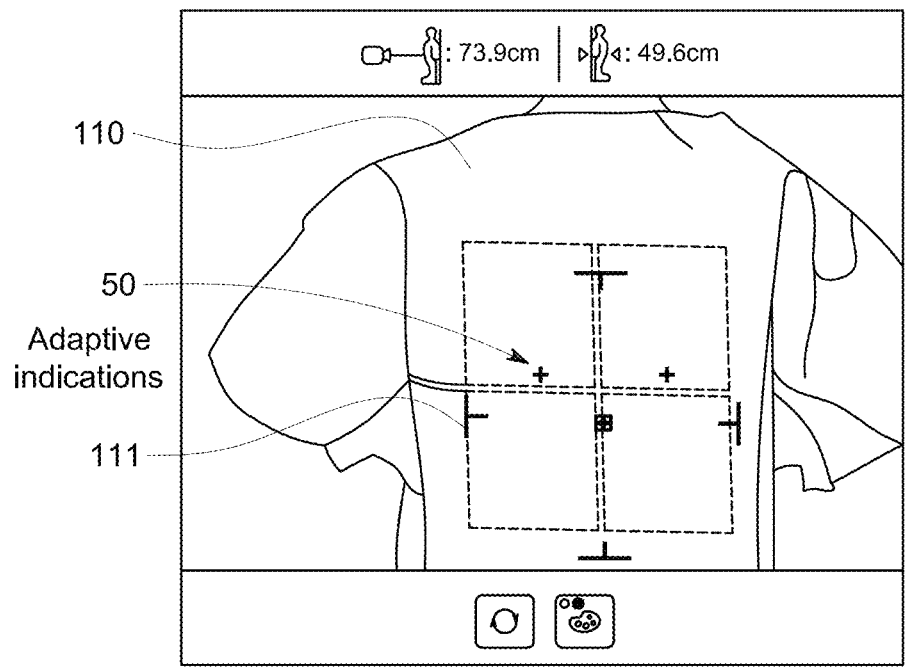

In the situation of step 318 where the image processing circuitry 28 and/or the AI system 100 classifies the camera image 46 as a monochromatic or quasi-monochromatic background, in order to determine the complementary color 111 for the detected dominant color 110, the image processing circuitry 28 and/or the AI system 100 references a color chart 116, which can be stored in database 29, where the dominant color 110 is matched with the associated complementary color 111, or can select the white as the complementary color 111. The overlay 48 is then created by the image processing circuitry 28 and/or the AI system 100 using the selected complementary color 111 to identify one or more of a central point 52 of the field of view (FOV) of the imaging system 10, the border 54 or boundary 108 of the detector 24, and/or the locations 56 of other components of the imaging system 10 positioned behind the patient 14, such as an ionization chamber, and presented on the display 40 along with the camera image 46. With reference to FIGS. 7A and 7C, a monochromatic camera image 46 is illustrated in FIG. 7A with an overlay 48 presented in a conventional or default color 115, such as blue or cyan, contrasted with the same camera image 46 shown in FIG. 7C but presented with an overlay 48 in a complementary color 111 relative to the dominant color 110 forming the background in the camera image 46 as determined by the image processing circuitry 28 and/or the AI system 100 of the present disclosure.

Figure 7D:
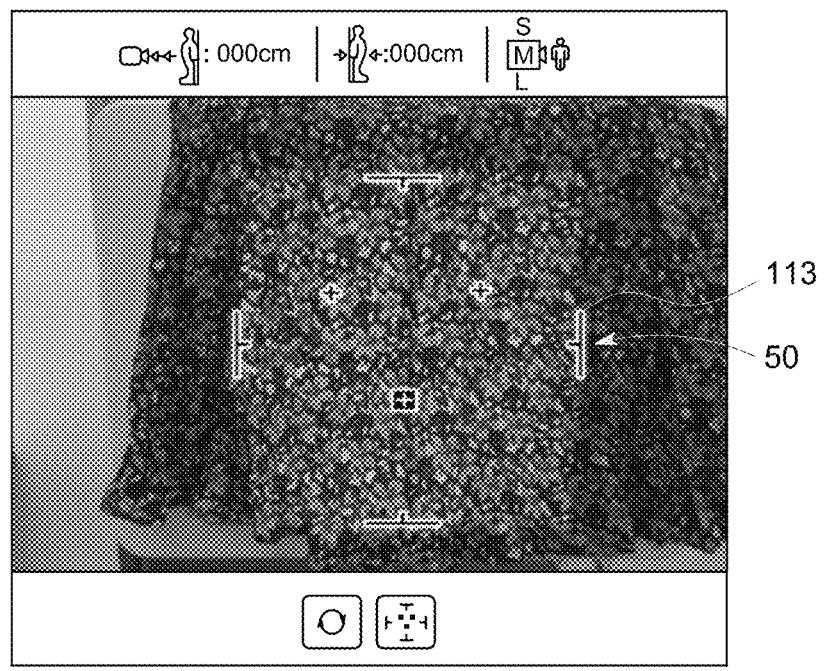

In the situation of step 320 where the image processing circuitry 28 and/or the AI system 100 classifies the camera image 46 as a chromatic background, the image processing circuitry 28 and/or the AI system 100 selects a high contrast color 113. The overlay 48 is then created by the image processing circuitry 28 and/or the AI system 100 using the high contrast color 113 to identify one or more of a central point 52 of the field of view (FOV) of the imaging system 10, the border 54 or boundary 108 of the detector 24, and/or the locations 56 of other components of the imaging system 10 positioned behind the patient 14, such as an ionization chamber, and presented on the display 40 along with the camera image 46. With reference to FIGS. 7B and 7D, a chromatic camera image 46 is illustrated in FIG. 7B with an overlay 48 presented in a conventional or default color 115, such as blue or cyan, contrasted with the same camera image 46 shown in FIG. 7D but presented with an overlay 48 in a high contrast color 113 relative to the dominant colors 110 forming the background in the camera image 46 as determined by the image processing circuitry 28 and/or the AI system 100 of the present disclosure.

Figure 8A:
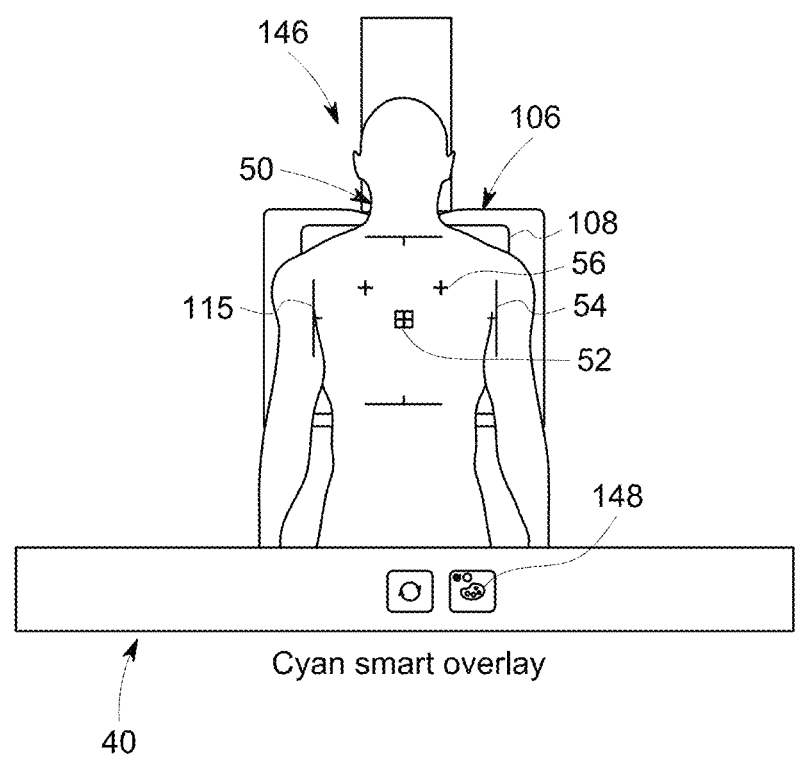
FIGS. 8A-8B are schematic views of the camera image and overlay formed by adaptive user interface overlay display system on a user interface according to an exemplary embodiment of the disclosure.
Figure 8B:
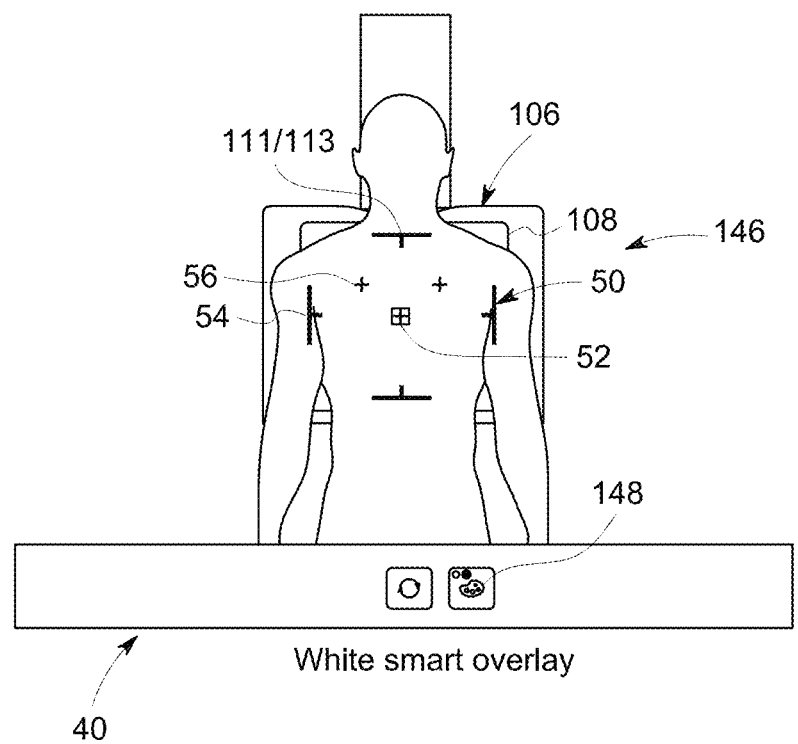

Referring now to FIGS. 8A and 8B, in another exemplary embodiment of the image processing circuitry 28 and/or the AI system 100 of the present disclosure, the operation of the image processing circuitry 28 and/or the AI system 100 can be performed prior to and/or during the presentation of the camera image 46 on the display 40. For example, in FIG. 8A, a schematic view of a camera image 146 illustrated on a display 40 is shown. The camera image 46 is initially presented on the display 40 with an overlay 48 having a conventional or default color 115. In reviewing the camera image 46 and overlay 48, should the user determine that the overlay 48 is not readily discernable on or within the camera image 46, the user can select an overlay adjustment button 148 presented on the display 40 in conjunction with the camera image 46. By selecting the button 148 in a suitable manner with a user input device 38, such as by positioning a cursor (not shown) over the button and selecting the button 148 through the use of a mouse (not shown), the user can enable the image processing circuitry 28 and/or the AI system 100 to provide an overlay 48 on the display 40 for the camera image 46 with a color corresponding to a complementary color 111 and/or a high contrast color 113 relative to the dominant color(s) 110 forming the background of the camera image 46, such as shown in FIG. 8B. In providing the overlay 48 with the complementary color 111 and/or a high contrast color 113, the image processing circuitry 28 and/or the AI system 100 can provide the overlay 48 with a complementary color 111 and/or a high contrast color 113 determined by the operation of the image processing circuitry 28 and/or the AI system 100 either prior to the presentation of the camera image 46 on the display 40, and/or after the presentation of the camera image 46 on the display 40.

Further, the button 148 can be selected as desired to toggle between an overlay formed of the conventional or default color 115 and the complementary color 111 and/or a high contrast color 113 by subsequent selections of the button 148. Also, according to another exemplary embodiment of the disclosure, a subsequent selection of the button 148 can indicate to the image processing circuitry 28 and/or the AI system 100 that the selected complementary color 111 and/or a high contrast color 113 is not adequately illustrating the overlay 48 on the camera image 46 to the user, e.g., if the selected or first complementary color 111 and/or a high contrast color 113 is green or red and the user is colorblind, such that the image processing circuitry 28 and/or the AI system 100 can proceed to select another or second complementary color 111 and/or a high contrast color 113 more discernable by the particular user.

With the capability of the image processing circuitry 28 and/or the AI system 100 to adaptively select a complementary color 111 and/or a high contrast color 113 for an overlay 48 presented within a camera image 46 having a monochromatic or chromatic background, the overlay 48 and indications 50 contained therein can be clearly displayed under different real-time situations, even in some challenging cases. Further, the process employed by the image processing circuitry 28 and/or the AI system 100 for the selection and presentation of the overlay 48 in the complementary color 111 and/or a high contrast color 113 for the camera image 46 is completely automatic, fast and intelligent without requiring input or subjective perception from a user. Further, in other alternative embodiments, the image processing circuitry 28 and/or the AI system 100, or the user can selectively alter the presentation color 111,113 of individual indications 50 of the overlay 48 according to the previously described system and method in order to enhance the ability of the user to discern indications 50 disposed over different portions of the ROI 106 which may have different dominant colors 110 therein.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method for adaptively adjusting a presentation color of an overlay in conjunction with a camera image presented on a user interface of a radiography imaging system, the method comprising the steps of:
   a. providing an imaging system comprising:
      i. a radiation source;
      ii. a detector alignable with the radiation source, the detector having a support on or against which a subject to be imaged is adapted to be positioned;
      iii. a camera aligned with the detector;
      iv. a control processing unit operably connected to the radiation source and detector to generate image data in an imaging procedure performed by the imaging system, and to the camera to generate camera images, the control processing unit including image processing circuitry and an interconnected database for processing the image data from the camera to create one or more camera images of the detector;
      v. a display operably connected to the controller for presenting information to a user; and
      vi. the user interface operably connected to the control processing unit to enable user input to the control processing unit;
   b. positioning a subject between the radiation source and the detector;
   c. operating the camera to generate a camera image of at least one of the subject, the detector and combinations thereof;
   d. determining an ROI within the camera image;
   e. determining a dominant color of the ROI; and
   f. adjusting a presentation color of an overlay presented with the camera image on the display in relation to the dominant color of the ROI.

2. The method of claim 1, wherein the step of determining the ROI within the camera image comprises determining a boundary of the detector as the ROI within the camera image.

3. The method of claim 1, wherein the step of determining the ROI in the camera image comprises determining a boundary of the subject covering a portion of the detector as the ROI within the camera image.

4. The method of claim 3, wherein the step of determining a boundary of the subject covering a portion of the detector as the ROI within the camera image comprises the steps of:
   a. generating a depth image of the detector and the subject with a depth sensor on the imaging system;
   b. matching the depth image with the camera image; and
   c. determining the boundary of the subject over the detector.

5. The method of claim 4, wherein the camera is an RGB-D camera.

6. The method of claim 1, wherein the step of determining the dominant color in the ROI comprises the steps of:
   a. identifying all colors present in the ROI;
   b. identifying one or more dominant colors from all colors within the ROI.

7. The method of claim 6, wherein the step of identifying all colors within the ROI comprises generating a color map of all pixels within the camera image.

8. The method of claim 7, wherein the step of identifying all colors within the ROI comprises the step of clustering pixels of the color map within predetermined ranges of individual colors.

9. The method of claim 6, wherein the step of identifying the one or more dominant colors in the ROI comprises identifying individual colors exceeding a threshold for an amount of pixels within the camera image.

10. The method of claim 6, wherein the step of identifying the one or more dominant colors in the ROI comprises identifying individual colors exceeding a threshold for a percentage of pixels within the camera image.

11. The method of claim 6, wherein the step of adjusting the presentation color of an overlay comprises adjusting the presentation color to a complementary color when a single dominant color is identified in the ROI.

12. The method of claim 6, wherein the step of adjusting the presentation color of an overlay comprises adjusting the presentation color to a high contrast color when multiple dominant colors are identified in the ROI.

13. The method of claim 1, further comprising the step of altering the presentation color of the overlay through the user interface after adjusting the presentation color of the overlay.

14. The method of claim 1, wherein the step of operating the camera to obtain the camera images comprises operating the camera to obtain streaming, real-time camera images.

15. The method of claim 1, wherein the image processing circuitry comprises an artificial intelligence (AI) rained to automatically determine the location of the ROI within the camera image, to automatically determine the dominant color in the ROI by identifying all colors present in the ROI, and to automatically adjust the presentation color to a complementary color when a single dominant color is identified in the ROI, or to a high contrast color when multiple dominant colors are identified in the ROI.

16. A radiography imaging system comprising:
 a. a radiation source;
 b. a detector alignable with the radiation source;
 c. a camera alignable with the detector;
 d. a control processing unit operably connected to the radiation source and detector to generate image data in an imaging procedure performed by the imaging system, and to the camera to generate camera images, the control processing unit including image processing circuitry and an interconnected database for processing the image data from the camera to create one or more camera images of the detector;
 e. a display operably connected to the controller for presenting information to a user; and
 f. a user interface operably connected to the control processing unit to enable user input to the control processing unit;
 wherein the image processing circuitry is configured to operate the camera to generate a camera image of at least one of a subject, the detector and combinations thereof, to determine an ROI within the camera image, to determine a dominant color of the ROI, and to adjust a presentation color of an overlay presented with the camera image on the display in relation to the dominant color of the ROI.

17. The radiography imaging system of claim 16, wherein the image processing circuitry is configured to determine the ROI within the camera image by one of determining a boundary of the detector as the ROI within the camera image or by determining a boundary of the subject covering a portion of the detector as the ROI within the camera image.

18. The radiography imaging system of claim 17, wherein the image processing circuitry is configured to determine the dominant color in the ROI by identifying all colors present in the ROI, and identifying one or more dominant colors from all colors within the ROI.

19. The radiography imaging system of claim 18, wherein the image processing circuitry is configured to adjust the presentation color of the overlay by one of adjusting the presentation color to a complementary color when a single dominant color is identified in the ROI, or adjusting the presentation color to a high contrast color when multiple dominant colors are identified in the ROI.

20. The radiography imaging system of claim 16, wherein the imaging processing circuitry includes an AI trained to automatically determine the location of the ROI within the camera image, to automatically determine the dominant color in the ROI by identifying all colors present in the ROI, and to automatically adjust the presentation color to a complementary color when a single dominant color is identified in the ROI, or to a high contrast color when multiple dominant colors are identified in the ROI.

* * * * *